United States Patent
Frendl et al.

(10) Patent No.: US 9,629,713 B2
(45) Date of Patent: Apr. 25, 2017

(54) BIOMEDICAL IMPLANT FOR USE IN FLUID SHEAR STRESS ENVIRONMENTS

(71) Applicant: CORNELL UNIVERSITY, Ithaca, NY (US)

(72) Inventors: Christopher M. Frendl, Southborough, MA (US); Jonathan T. Butcher, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 147 days.

(21) Appl. No.: 14/344,895

(22) PCT Filed: Sep. 17, 2012

(86) PCT No.: PCT/US2012/055732
§ 371 (c)(1),
(2) Date: Mar. 13, 2014

(87) PCT Pub. No.: WO2013/040544
PCT Pub. Date: Mar. 21, 2013

(65) Prior Publication Data
US 2014/0350671 A1 Nov. 27, 2014

Related U.S. Application Data

(60) Provisional application No. 61/535,260, filed on Sep. 15, 2011.

(51) Int. Cl.
*A61F 2/06* (2013.01)
*A61F 2/24* (2006.01)
(Continued)

(52) U.S. Cl.
CPC ............. *A61F 2/24* (2013.01); *A61F 2/06* (2013.01); *A61F 2/82* (2013.01); *A61L 27/3804* (2013.01);
(Continued)

(58) Field of Classification Search
USPC ........................................................ 623/1.29
See application file for complete search history.

(56) References Cited

U.S. PATENT DOCUMENTS 4,553,272 A   11/1985 Mears
4,828,563 A   5/1989 Muller-Lierheim
(Continued)

FOREIGN PATENT DOCUMENTS

WO   02/071975 A2   9/2002
WO   2008/061185 A1   5/2008

OTHER PUBLICATIONS

International Search Report and Written Opinion issued in PCT/US2012/055732, mailed Feb. 28, 2013.
(Continued)

*Primary Examiner* — Katrina Stransky
*Assistant Examiner* — Wade P Schutte
(74) *Attorney, Agent, or Firm* — FisherBroyles, LLP; Andrew K. Gonsalves, Esq.

(57) ABSTRACT

The present invention relates to a biomedical implant for use in a fluid shear stress environment of a subject. The biomedical implant of the present invention includes a patterned surface having a plurality of cellular niches. The cellular niches of the patterned surface are effective to maintain at least one localized layer of living cells within the plurality of cellular niches by decreasing fluid shear stress within the cellular niches as compared to fluid shear stress measured outside of the cellular niches, with the fluid shear stress measured outside of the cellular niches having a peak fluid shear stress of at least about 50 dynes per square centimeter (dynes/cm$^2$). The present invention also relates to methods of making and using the biomedical implant. The present invention further relates to a biomedical implant system.

11 Claims, 8 Drawing Sheets

(51) Int. Cl.
　　　A61L 27/38　　　(2006.01)
　　　A61L 27/50　　　(2006.01)
　　　A61L 31/14　　　(2006.01)
　　　A61F 2/82　　　(2013.01)
(52) U.S. Cl.
　　　CPC .............. *A61L 27/50* (2013.01); *A61L 31/14* (2013.01); *A61F 2240/001* (2013.01)

(56) References Cited

U.S. PATENT DOCUMENTS

| | | |
|---|---|---|
| 5,455,040 A | 10/1995 | Marchant |
| 6,033,582 A | 3/2000 | Lee et al. |
| 6,214,407 B1 | 4/2001 | Laube et al. |
| 9,138,512 B2 * | 9/2015 | Ferrari .................. A61L 31/022 |
| 2002/0095219 A1 | 7/2002 | Nelles et al. |
| 2007/0077649 A1 | 4/2007 | Sammak et al. |

OTHER PUBLICATIONS

International Preliminary Report on Patentability issued in PCT/US2012/055732, mailed Mar. 18, 2014.

Likibi et al., "Biomimetic nanocoating promotes osteoblast cell adhesion on biomedical implants," *Journal of Materials Research*, 23(12):3222-3228 (2008).

Roessler et al., "Biomimetic coatings functionalized with adhesion peptides for dental implants," *Journal of Materials Science: Materials in Medicine*, 12:871-877 (2001).

Murtuza et al., "Micro- and nanoscale control of the cardiac stem cell niche for tissue fabrication," *Tissue Engineering*, 15(4):443-454 (2009).

\* cited by examiner

BIOMEDICAL IMPLANT FOR USE IN FLUID SHEAR STRESS ENVIRONMENTS

CROSS-REFERENCE TO RELATED APPLICATIONS

This application is a U.S. National Phase filing under 35 U.S.C. §371 of International Application No. PCT/US2012/055732, filed Sep. 17, 2012, and published as WO 2013/040544-A2 on Mar. 21, 2013, which claims benefit of priority from U.S. Provisional Patent Application Ser. No. 61/535,260, filed Sep. 15, 2011. The entire contents of each of the prior applications are incorporated herein by reference in their entirety.

FIELD OF THE INVENTION

The present invention relates to a biomedical implant and a biomedical implant system for use in a fluid shear stress environment of a subject. The present invention also relates to a method for maintaining at least one localized layer of living cells on a biomedical implant introduced into a fluid shear stress environment of a subject.

BACKGROUND OF THE INVENTION

Various technologies have been described in the art that involve promoting cell growth on the surface of biomedical implants. Examples of such technologies include (i) nanocoating of implant materials and (ii) porous scaffold based devices. However, these technologies are deficient in various aspects.

Nanocoating of Implant Materials:

This strategy utilizes the ability to nano fabricate a surface coating onto implanted devices which can act as the anchoring for cellular growth on the device surfaces. Made of bio-compatible materials, cell adhesion is promoted by surface structures and cell interaction with the coating. Electro-coating is often utilized to ensure a strong adhesion of the coating to the implantable device. The coating can be made from polypeptides or any material that may enhance cell adhesion and growth.

Porous Scaffold Based Devices:

The use of porous scaffolds has been developed to allow for cells or growth factors to be incorporated into implantable devices. This technique impregnates the device with pores that have a specific size depending on the desired applications. While this application allows molecules or cells to be incorporated into the structure, the entire device is a porous material, detracting from the integrity of the device.

Endothelial cells line blood contacting surfaces of the cardiovascular system, transducing hemodynamic signals and maintaining a non-thrombogenic surface. The drawback of many cardiovascular implants is the necessity for concurrent administration of anti-coagulant therapies. These implants require these drugs due to foreign surfaces contacting circulating blood components. Specifically, the blood-device interaction promotes platelet and clot aggregation on the device surface, rendering it a medical hazard. By thinning the blood with anticoagulants, patients are able to benefit from cardiac implants such as heart valves and stents without having to worry about clotting or platelet aggregation on their implanted cardiac devices. The drawback to taking blood-thinners is the altered capacity of blood. Patients taking blood thinners have a difficult time clotting when injured. Individuals needing cardiac implants are required to have a limited lifestyle upon treatment, dramatically reducing quality of life. This includes the inability to get pregnant, vast reduction in physical activity, and high risk of bleeding. Endothelial cells naturally regulate the blood clotting cascade (1). Coating the surfaces of these implanted devices with endothelial cells would prevent the need for anticoagulants as the passing blood would not be able to differentiate the endothelial coated implant from healthy vasculature. The biological coating of cardiac implants assists in maintaining a natural hemodynamic environment, one that is protected by endothelial cells, preventing or decreasing the need for anti-thrombotic drugs.

Clot formation occurs naturally by platelet aggregation, followed by clotting cascade initiation. Platelets are recruited to the injury sites via two separate pathways; the collagen and tissue factor pathways. The mechanism of collagen initiated platelet aggregation is dependent upon glycoprotein VI, and glycoprotein Ib (2). Endothelial secreted factors such as TFPI and PECAM-1 (3, 4).

Currently there are two types of aortic heart valve replacements available to patients in need of a new valve. One option is the biological valve, which is the implantation of another valve either from a different part of the heart, a cadaver or an animal; while the other option is a mechanical valve. Each of these options has a drawback; the biological valves degrade over time and need to be replaced, while patients that choose to have the mechanical valves need to take blood thinners as they are susceptible to blood clots. Further, patients on blood thinners face the significant potential for major hemorrhages because of the lack of clotting.

The present invention is directed to overcoming these and other deficiencies in the art.

SUMMARY OF THE INVENTION

In one aspect, the present invention relates to a biomedical implant for use in a fluid shear stress environment of a subject. The biomedical implant of the present invention includes a patterned surface having a plurality of cellular niches. The cellular niches of the patterned surface are effective to maintain at least one localized layer of living cells within the plurality of cellular niches by decreasing fluid shear stress within the cellular niches as compared to fluid shear stress measured outside of the cellular niches, with the fluid shear stress measured outside of the cellular niches having a peak fluid shear stress of at least about 50 dynes per square centimeter (dynes/cm$^2$).

In another aspect, the present invention relates to a biomedical implant system for use in fluid shear stress environments of a subject. The biomedical implant system includes: (i) a biomedical implant according to any one of the biomedical implants of the present invention; and (ii) a plurality of cells seeded on at least a portion of the patterned surface of the biomedical implant, where the plurality of cells can be the same or different types of cells.

In another aspect, the present invention relates to a method for producing a biomedical implant for use in fluid shear stress environments of a subject. This method involves the following steps: (i) providing an implantable body having a substantially smooth surface; and (ii) modifying the substantially smooth surface into a patterned surface having a plurality of cellular niches effective to maintain at least one localized layer of living cells within the plurality of cellular niches by decreasing fluid shear stress within the cellular niches as compared to fluid shear stress measured outside of the cellular niches, where the fluid shear stress measured outside of the cellular niches has a peak fluid shear stress of at least about 50 dynes per square centimeter (dynes/cm²), thereby yielding the biomedical implant for use in fluid shear stress environments.

In another aspect, the present invention relates to a method for maintaining at least one localized layer of living cells on a biomedical implant introduced into a fluid shear stress environment of a subject. This method involves the following steps: (i) providing a biomedical implant according to any one of the biomedical implants of the present invention; (ii) seeding the patterned surface with cells of interest so that the cells form at least one localized layer of living cells within the plurality of cellular niches of the biomedical implant; and (iii) introducing the seeded biomedical implant into a fluid shear stress environment of the subject so as to maintain the at least one localized layer of living cells within the plurality of cellular niches by decreasing fluid shear stress within the cellular niches as compared to fluid shear stress measured outside of the cellular niches, where the fluid shear stress measured outside of the cellular niches has a peak fluid shear stress of at least about 50 dynes per square centimeter (dynes/cm²).

One advantage of the present invention is that it provides geometric modification of surfaces of biomedical devices to promote cellular adhesion, cellular survival, cellular proliferation, and to improve biological function. In one example, the present invention provides cellular niches on the surfaces of biomedical implants to protect and enhance cell growth for applications in which cellular coatings are currently unavailable due to shear stress exposure. Fluid flows induce high shear stresses and prevent cellular coatings of biomedical devices. While the highest fluid shear stress in the body is in the aortic valve, renal filtration offers a smaller scale version of a similar phenomenon. The present invention is effective to lower the shear stresses on the majority of the implant surface, creating a cell friendly environment. Coating cardiovascular and renal filtration devices could have a great impact medically as patients would not require the current dosage of anti-coagulant drug therapies and would be able to resorb nutrient loss due to dialysis. The present invention allows for the cellular coating of biomedical devices in fluid shear exposed environments by creating a protected niche where cells can proliferate and interact biologically with their surroundings, increasing implant functionality and improving patient quality of life.

The cellular niches of the present invention also are effective to protect adhered cells from fluid derived mechanical forces while simultaneously enabling their robust secretion of soluble factors. Many implanted and extracorporeal biomedical devices are in contact with flowing blood. Receiving and providing signals through this medium is of critical importance, but shielding the sensory elements from potentially damaging shear stresses has been a continual challenge. Prominent examples include prosthetic heart valves, left-ventricular assist devices, and renal filtration systems. The present invention overcomes these limitations by creating mechanically protected niche environments where adherent cells can restore and maintain homeostasis. Further, the present invention provides micropatterned surfaces for local control of hemodynamic properties on biomedical implants.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 4A, carbon coated etched silicon; FIG. 4B, collagen; FIG. 4C, fibronectin; FIG. 4D, collagen+ PAVEC; FIG. 4E, fibronectin+PAVEC; FIG. 4F, collagen+ PAVEC+shear; and FIG. 4G, fibronectin+PAVEC+shear.

FIGS. 5A, 5B, and 5C: fibronectin coated chips with 10, 20, and 2 dynes/cm² of shear; FIG. 5D: collagen exposed to 2 dynes/cm² of shear for 48 hours.

FIG. 10A: flow velocity of blood over the surface of the optimized valve; FIG. 10B: shear stresses exerted on the surface of the valve and within the wells of the etched channels.

FIG. 13A: initial cell density prior to shear exposure; FIG. 13B: cell presence after 20 minutes of shear at 80 ml/min.

FIG. 14A: VE-Cadherin (Vascular Endothelial) tagged red on the cell, showing endothelial phenotypes. FIG. 14B: eNOS (endothelial Nitric Oxide Synthase) green, showing that there are anti-thrombotic capabilities of the cell type. FIG. 14C: Cells with all three stains, i.e., VE-Cadherin, eNOS green, and Hoechst (nuclear cell stain blue) generic cell marker.

DETAILED DESCRIPTION OF THE INVENTION

The present invention generally relates to, inter alia, devices, systems, and methods that enable the use of a biomedical implant in a fluid shear stress environment of a subject. The present invention also generally relates to, inter alia, devices, systems, and methods that enable the use of a biomedical implant in maintaining at least one localized layer of living cells on the biomedical implant when introduced into a fluid shear stress environment of a subject. One advantage of the biomedical implant and biomedical implant system of the present invention is that they can eliminate or significantly decrease the need for the administration of various medications or drug regimens that are typically used in implantation surgeries in fluid shear stress environments, such as the use of blood thinning anticoagulants in heart valve and stent implantations.

Figure 3:
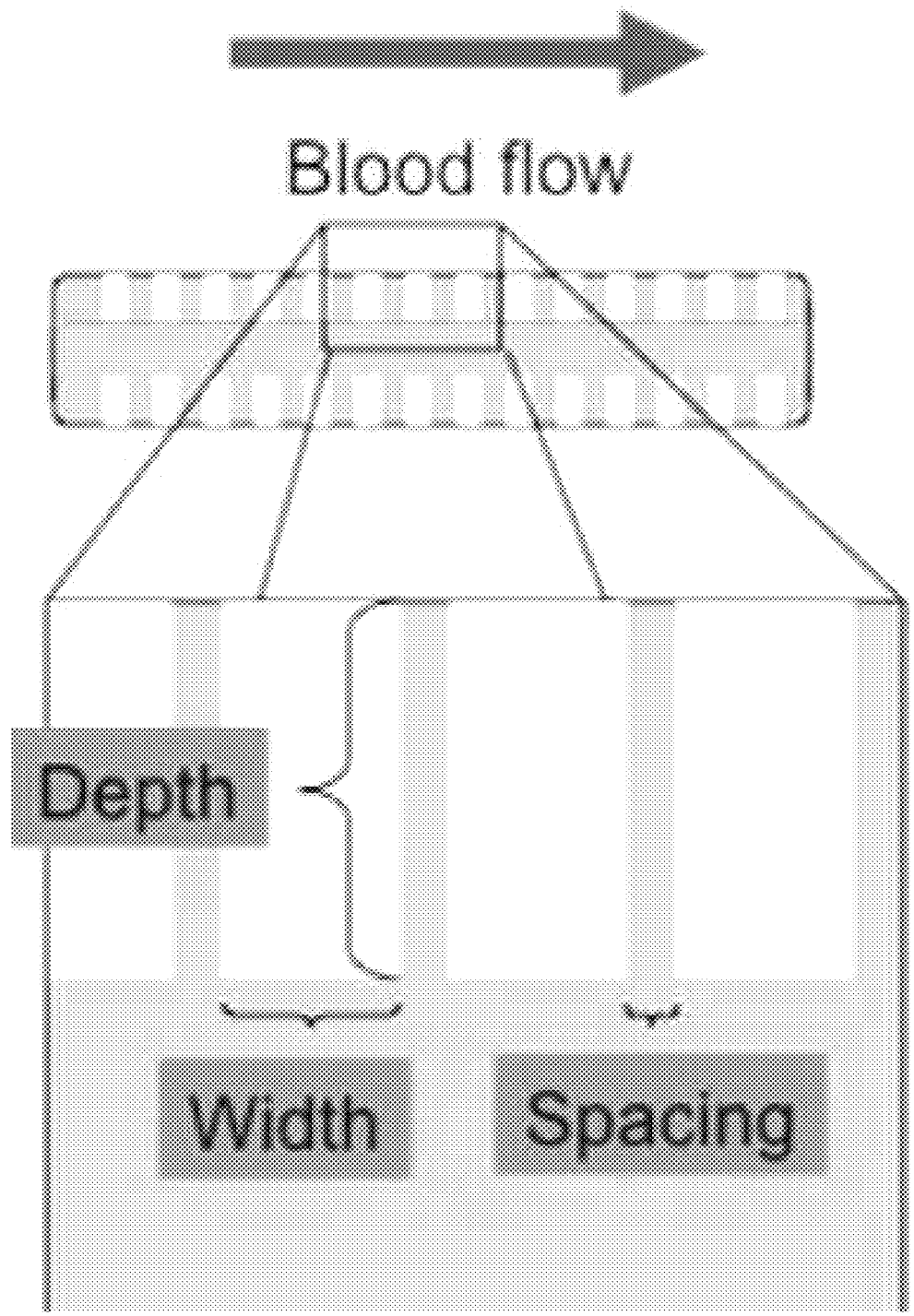
FIG. 3 is a diagram showing a cross sectional view of one embodiment of an etched prosthetic heart valve concept of the present invention.
Figure 7:
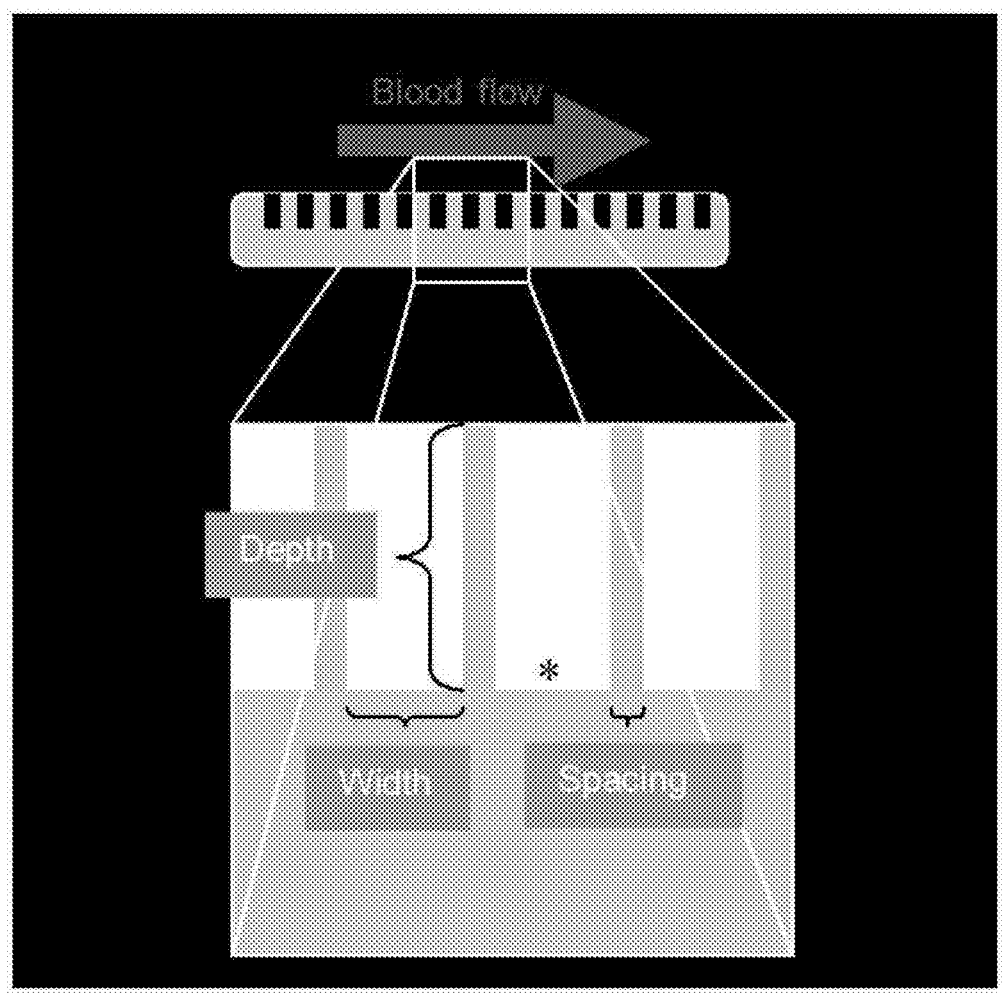
FIG. 7 is a diagram depicting one embodiment of geometry to be optimized for decreasing the shear stress at the bottom of the valve surfaces (depicted by *).

In a particular aspect, the present invention provides a biomedical implant that includes surface modifications that are effective in providing cellular niches that are able to maintain viable cells and other non-cell agents (i.e., any agent that is not a cell but that can be introduced into a subject) under fluid shear stress environments in a subject, even if the peak fluid shear stress in the environment reaches up to about 2,000 dynes per square centimeter (dynes/cm$^2$). As set forth in more detail herein, the present invention provides a means for designing the particular surface modifications to customize and/or optimize cell growth surface area of the cellular niches. These surface modifications take into account the depth of the cellular niches, the width of the cellular niches, the spacing between the cellular niches, and the interior geometry of the cellular niches in order to design desired three-dimensional configurations and placement of the cellular niches on a biomedical implant for its particular use. Illustrative examples of how to measure the depth, width, and spacing of the cellular niches of the present invention are shown in FIG. 3 and FIG. 7. Further, as described herein, the cellular niches of the biomedical implant can be configured with an interior shape so that viable cells and other non-cell agents can be maintained in the bottom of the cellular niche as well as on the sidewalls of the cellular niche, thereby maximizing surface growth and maintenance area of the cells and/or other non-cell agents.

In one aspect, the present invention relates to a biomedical implant for use in a fluid shear stress environment of a subject. The biomedical implant of the present invention includes a patterned surface having a plurality of cellular niches. The cellular niches of the patterned surface are effective to maintain at least one localized layer of living cells within the plurality of cellular niches by decreasing fluid shear stress within the cellular niches as compared to fluid shear stress measured outside of the cellular niches, with the fluid shear stress measured outside of the cellular niches having a peak fluid shear stress of at least about 50 dynes per square centimeter (dynes/cm$^2$). Techniques, instrumentation, materials, and protocols for measuring peak and average fluid shear stress in both in vitro models and in vivo locations are well known by those of ordinary skill in the art, including the period of time for measuring fluid shear stress. For example, fluid shear stress peaks and averages in one particular fluid shear stress environment can be measured for as little as 1 hour or less when designing the cellular niches for one particular biomedical implant (e.g., a hemofiltration device for dialysis), and as much as 48 hours or more when designing the cellular niches for another particular biomedical implant (e.g., a heart valve).

As used herein, the term "subject" is meant to include any mammal or non-mammal that can accept a biomedical implant placed into a fluid shear stress environment of the subject. Therefore, the term "subject" includes humans, land animals (e.g., dogs, cats, horses, cows, goats, etc.), aquatic animals, birds, fish, etc.

The biomedical implant of the present invention includes any type of implant suitable for implantation into a subject, as defined herein. Suitable examples of such implants include, without limitation, a heart valve (e.g., a prosthetic heart valve, a biological heart valve), a device for pancreatic regulation of insulin, a hemofiltration device, a catheter delivered blood contacting device, a stent, a prosthetic vascular graft, a cardiovascular patch, and the like. Further, as used herein, the term heart valve includes any valve that can be implanted into a subject in place of the subject's aortic valve, pulmonary valve, mitral valve, or tricuspid valve, whether the subject's heart valve to be replaced is defective, diseased, or substantially normal (e.g., to provide longer working life of a normal or substantially normal valve when replacing another valve of the same subject).

The biomedical implant of the present invention can include a plurality of cellular niches, as described herein. As used in this context, the term "plurality" means at least two different cellular niches formed into the surface of the biomedical implant. These at least two different cellular niches can have the same or different dimensions (as described herein) and the same or different configuration (e.g., interior geometry or linear formation). The number of different cellular niches formed into the surface of a particular biomedical implant can be determined by one of ordinary skill in the art depending on the type of biomedical implant or desired parameters and surface area for cell growth.

In one embodiment, each cellular niche of the biomedical implant is a crevice formed into the surface of the biomedical implant. As used herein, the term "crevice" refers to a furrow or trench below the surface of the biomedical implant. The crevice has a top, open end located at the surface of the biomedical implant; a bottom, substantially closed end located at the region furthest below the surface of the biomedical implant; and opposing sidewalls that extend from the top end to the bottom end of the crevice. As noted herein, one advantage of the crevice of the present invention is that the cells and/or non-cell agents can be maintained and retained not only at the bottom of the crevice, but also on one or both sidewalls of the crevice. This feature provides more overall surface area for the cells and non-cell agents as compared to surface channels in the art that are only able to maintain and retain cells on the bottom of their surface channels.

The crevice can have a length that runs the entire length of the surface of the biomedical implant or just a portion of the length of the surface of the biomedical implant. Further, the crevice can include gaps along the surface of the biomedical implant, with the gaps being solid portions at the surface of the biomedical implant. In such an arrangement, the crevice may or may not have openings below the surface that connect one crevice to another crevice either in an end-to-end or side-to-side fashion. In addition, the crevice can have an interior surface that is solid, substantially solid, porous, or a combination thereof. Porous interior surfaces are designed so that agents (organic and/or inorganic agents) contained within one crevice can pass through more or more pores in that crevice and into an adjacent crevice through the adjacent crevice's pores. For example, cells in one crevice could release an agent that passes to an adjacent crevice through the respective pores of the crevices. In one embodiment, the crevice is either closed, open, or partially open at one or both of its lengthwise ends. However, the present invention contemplates any type of formation or configuration at the lengthwise ends of the crevices of the present invention. For example, the ends of the plurality of cellular niches (i.e., crevices) can terminate in a perpendicular or substantially perpendicular row so that the row operates as an end wall to each cellular niche. As can be readily understood by one of ordinary skill in the art, the term "crevice" is used interchangeably with the term "cellular niche" herein.

In one embodiment, the cellular niches of the biomedical implant of the present invention may be formed into the surface of the biomedical implant so that they run perpendicular or substantially perpendicular to fluid flow when the biomedical implant is implanted in the appropriate working manner in a subject. In other words, in such a configuration, fluid flow and the generated fluid shear stress will be applied across the cellular niche or crevice of the patterned surface of the biomedical implant.

In another embodiment, the cellular niches of the biomedical implant of the present invention may be formed into the surface of the biomedical implant so that they run parallel or substantially parallel to fluid flow when the biomedical implant is implanted in the appropriate working manner in a subject. In other words, in such a configuration, fluid flow and the generated fluid shear stress will be applied along the cellular niche or crevice of the patterned surface of the biomedical implant.

In another embodiment, the cellular niches of the biomedical implant of the present invention may be formed into the surface of the biomedical implant so that they run at a substantially linear manner at an angle that is somewhere between perpendicular and parallel to fluid flow when the biomedical implant is implanted in the appropriate working manner in a subject. In other words, in such a configuration, fluid flow and the generated fluid shear stress will be applied at an angle that is greater than 0° degrees and less than 90° to the cellular niche or crevice of the patterned surface of the biomedical implant when fluid flow is moving in one direction relative to the cellular niche or crevice, or at an angle that is greater than 90° degrees and less than 180° to the cellular niche or crevice of the patterned surface of the biomedical implant when fluid flow is moving in the opposite direction relative to the cellular niche or crevice.

The cellular niches of the biomedical implant of the present invention may also be configured to have the same or different types of bottom end topographical conformations. Suitable bottom end topographical conformations of the cellular niche can be substantially planar surfaces or non-planar surfaces, including, without limitation, a flat surface, a concave surface, a convex surface, a filleted surface, a chamfered edged surface, a curved edged surface, and combinations thereof. Therefore, the cellular niches can have an interior geometric shape, configuration, or formation that includes fully hemispherical to fully triangular bottom ends, as well as completely flat bottom ends. Further, the bottom end topographical conformation within a single cellular niche can also be the same or variable. For example, in embodiments having chamfers and/or fillets, the chamfers and/or fillets can vary between 0 and 50% of the width of the cellular niche. Thus, with respect to cellular niches having multiple chamfers or fillets, such multiple chamfers or fillets can be at the top and/or bottom ends, as well as along each opposing sidewall or along just one sidewall or just portions of the sidewalls.

The crevice of the biomedical implant of the present invention may also have a width that is the same or that varies. The width of a crevice at a particular location is the distance measured from one location on one sidewall of the crevice to a corresponding location on the opposing sidewall of the same crevice. However, as noted, because the width of a crevice can be the same or vary, the width measured between opposing sidewalls of a given crevice can be the same or different throughout the length and/or height of that crevice. Further, different crevices formed into the surface of a biomedical implant can be the same or different in terms of dimension (depth, width, and length) and pattern.

With respect to suitable dimensions for the crevices of the present invention, a crevice can have a depth of between about 100-1500 microns (μm), a width of between about 100-1000 μm, and any length that spans all or a portion of the surface of a biomedical implant when measured from one side of the biomedical implant to the opposite side of the biomedical implant.

Spacing between cellular niches of the biomedical implant can range from between about 1-600 μm. Unless otherwise specified, the spacing between cellular niches means the spacing as measured at the surface of the biomedical implant between adjacent cellular niches, with the spacing being substantially the same along the lengths of the two adjacent cellular niches. However, the present invention also provides that the spacing between adjacent cellular niches can vary along the length of the adjacent cellular niches as well as along the depth of the adjacent cellular niches (i.e., the height measured from top to bottom). For example, the width between adjacent cellular niches will change along their depths (i.e., from top end to bottom end of the crevice) as the width of a given crevice changes.

As described herein, a unique feature of the biomedical implant of the present invention is that the surface modifications (i.e., the cellular niches) are designed with the following parameters in mind: depth of the cellular niche; width of the cellular niche; and spacing between each cellular niche. In addition, the present invention provides a means for determining each particular dimension for the plurality of cellular niches (i.e., depth, width, and spacing) in order to form a patterned surface on the biomedical implant that has a desired growth area for the cells or non-cell agents maintained within the cellular niches of that patterned surface.

Figure 8:
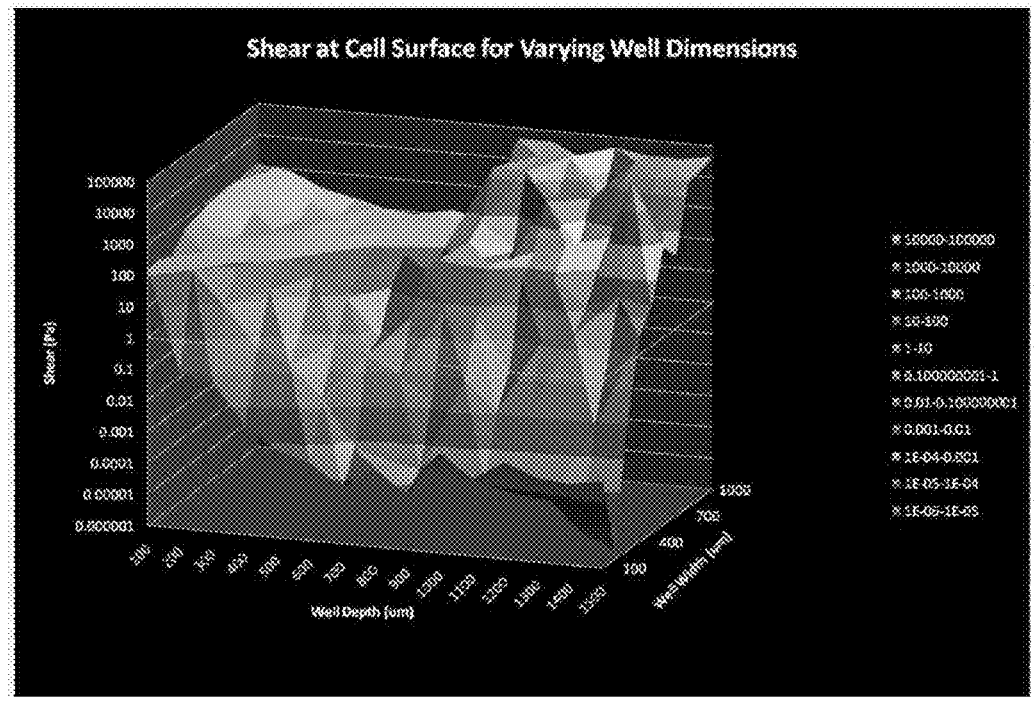
FIG. 8 is a graphical depiction of shear stress measured at the bottom of two dimensional wells for different depths and widths.

In one embodiment, depending on the desired decrease in fluid shear stress within the cellular niches as compared to fluid shear stress outside of the cellular niches, the dimensions of the cellular niche can be determined by using the graph set forth in FIG. 8. Further, one of ordinary skill in the art could use the graphical data set forth in FIG. 8 to readily develop a mathematical formula in order to calculate the desired cellular niche dimensions (particularly the depth and width of the cellular niches). Once the depth and width of the cellular niches are determined, one of ordinary skill in the art could determine the desired and/or optimal spacing between the plurality of cellular niches in order to yield the desired and/or maximal growth area for cells and/or non-cell agents within the cellular niches of a surface of a biomedical implant of the present invention.

According to one embodiment, the biomedical implant of the present invention includes a patterned surface of a plurality of cellular niches that are effective to decrease fluid shear stress within the cellular niches compared to fluid shear stress measured outside of the cellular niches, where the fluid shear stress measured outside of the cellular niches includes, but is not limited to, a peak fluid shear stress of greater than at least about 60 dynes/cm$^2$, greater than at least about 100 dynes/cm$^2$, greater than at least about 150 dynes/cm$^2$, greater than at least about 200 dynes/cm$^2$, greater than at least about 300 dynes/cm$^2$, greater than at least about 400 dynes/cm$^2$, greater than at least about 500 dynes/cm$^2$, greater than at least about 600 dynes/cm$^2$, greater than at least about 700 dynes/cm$^2$, greater than at least about 800 dynes/cm$^2$, greater than at least about 900 dynes/cm$^2$, greater than at least about 1,000 dynes/cm$^2$, greater than at least about 1,250 dynes/cm$^2$, greater than at least about 1,500 dynes/cm$^2$, greater than at least about 1,750 dynes/cm$^2$, and greater than at least about 2,000 dynes/cm$^2$.

According to another embodiment, the biomedical implant of the present invention includes a patterned surface of a plurality of cellular niches that are effective to decrease fluid shear stress within the cellular niches compared to fluid shear stress measured outside of the cellular niches, where the fluid shear stress measured outside of the cellular niches includes, but is not limited to, a peak fluid shear stress of between about 60-2,000 dynes/cm$^2$.

According to another embodiment, the biomedical implant of the present invention includes a patterned surface of a plurality of cellular niches that are effective to decrease peak fluid shear stress within the cellular niches to between about 5 and about 100 percent (%) of the peak fluid shear stress measured outside of the cellular niches. The present invention contemplates that the percent decrease of peak fluid shear stress within the cellular niches can be any value between the aforementioned about 5-100%; therefore, the particular percentages are not and need not be stated herein in order to be adequately described and enabled herein. For illustrative purposes, the plurality of cellular niches are effective to decrease peak fluid shear stress within the cellular niches to at least 5, 10, 15, 20, 25, 30, 35, 40, 45, 50, 55, 60, 65, 70, 75, 80, 85, 90, 95, 96, 97, 98, 99, and 99.5% of the peak fluid shear stress measured outside of the cellular niches.

When formed into the surface of the biomedical implant, the cellular niches may be arranged in a pattern that is uniform, substantially uniform, or non-uniform. As used herein, the term "uniform" refers to cellular niches that are spaced the same distance (i.e., spacing) from one another, i.e., the distance between adjacent cellular niches, and that have the same or substantially the same linear configuration or formation from end-to-end (lengthwise for each cellular niche). In some embodiments, as used herein, the term "uniform" refers to cellular niches that are spaced the same distance (i.e., spacing) from one another, that have the same or substantially the same width as one another, and that have the same or substantially the same linear configuration or formation from end-to-end (lengthwise for each cellular niche). A pattern of cellular niches can still be "uniform" whether the interior shape of each cellular niche is the same or different from one another. In a particular embodiment, "uniform" cellular niches are those that form a repeating pattern of cellular niches that have the same or substantially the same width and spacing there between and have the same or substantially the same linear configuration or formation from end-to-end (lengthwise for each cellular niche). In other embodiments, the biomedical implant of the present invention can have more than one different pattern of plurality of cellular niches. Thus, in one example, the patterned surface of the biomedical implant can have a group of cellular niches that are oriented in a different fashion from one or more of another group of cellular niches (e.g., parallel, perpendicular, and at an angle that is between parallel and perpendicular). Further, the cellular niches can be in a repeating pattern on a particular surface of the biomedical implant, thereby resulting in multiple sub-patterns of cellular niches.

The biomedical implant of the present invention can be made of any material suitable for implantation into a subject. For example, suitable materials for the biomedical implant of the present invention can include, without limitation, any biocompatible material or biocompatible coated material, a metal, a plastic, a polymeric material, glass, silicon, and the like.

Suitable techniques, materials, protocols, and instrumentation for forming the desired pattern of cellular niches into the surface of the biomedical implant of the present invention are known by those of ordinary skill in the art. In one embodiment, the cellular niches are formed into the surface of the biomedical implant using etching procedures. In other embodiments, in addition to etching, those of ordinary skill in the art can readily use standard protocols, materials, and techniques to form the cellular niches into the surface of the biomedical implant of the present invention using milling, machining, lithography, freeform fabrication, etc. Therefore, the present invention is not limited to a particular method of manufacturing the cellular niches of the biomedical implants of the present invention.

The biomedical implant of the present invention can also be coated with any coating material that is suitable for implantation into a subject (e.g., material that is known or believed to be known to not be at risk of being rejected by a particular subject targeted for implantation of the biomedical implant of the present invention). Suitable coating materials can include organic, inorganic, and/or bioactive materials. In particular, suitable coating materials can include, without limitation, a carbon (e.g., pyrolytic carbon), a metal, a metal alloy, synthetic polymer, silicon, and the like. Suitable techniques, materials, protocols, and instrumentation for coating the biomedical implant of the present invention are known by those of ordinary skill in the art.

As provided herein, the biomedical implant of the present invention includes a patterned surface having a plurality of cellular niches effective to maintain at least one localized layer of living cells within the plurality of cellular niches. As used herein, a "localized layer of living cells" is meant to include a layer of viable cells that form a continuous grouping of cells that are contained in a portion of a cellular niche. The present invention also provides for the maintenance of more than one localized layer of living cells, including layers of cells that substantially cover all or substantially all of the surface area of one or more cellular niche of the biomedical implant. The layer of cells can be in the form of a monolayer of a single type of cell or a monolayer of different types of cells. Further, the layer of cells can be in the form of multiple layers of a single type of cell or multiple layers of different types of cells. The various types of cells can include, without limitation, endothelial cells, endocardial cells, epithelial-like cells (e.g., cells like uroepithelial cells or renal epithelial cells), stem cells, progenitor cells, and the like. In certain embodiments, multiple types of cells can be included within the cellular niches of a particular biomedical implant in order to form a trans-cellular niche system so that one type of cell can communicate with another type of cell using cellular signaling, thereby inducing the cell to react in a certain way (e.g., release an inhibitor, enzyme, growth factor, etc.).

In one embodiment, the layer of cells can be a monolayer of one type of cell in all or substantially all of the crevices of the present invention. In another embodiment, the layer of cells can be a monolayer of two or more cell types in all or substantially all of the crevices of the present invention. In another embodiment, the layer of cells can be a monolayer overlying another monolayer in all or substantially all of the crevices of the present invention. In another embodiment, the layer of cells can be a monolayer of a first cell type in some crevices of a biomedical implant of the present invention, a monolayer of a second cell type in other crevices of the same biomedical implant of the present invention, and, optionally, more monolayers of additional cell types in other crevices of the same biomedical implant of the present invention, and any variations of such.

In another aspect, the present invention relates to a biomedical implant system for use in fluid shear stress environments of a subject. The biomedical implant system includes: (i) a biomedical implant according to any one of the biomedical implants of the present invention; and (ii) a plurality of cells seeded on at least a portion of the patterned surface of the biomedical implant, where the plurality of cells can be the same or different types of cells. The plurality of cells can be seeded on at least a portion of the patterned surface of the biomedical implant using materials, techniques, procedures, and instrumentation well known to those of ordinary skill in the relevant art.

In another aspect, the present invention relates to a method for producing a biomedical implant for use in fluid shear stress environments of a subject. This method involves the following steps: (i) providing an implantable body having a substantially smooth surface; and (ii) modifying the substantially smooth surface into a patterned surface having a plurality of cellular niches effective to maintain at least one localized layer of living cells within the plurality of cellular niches by decreasing fluid shear stress within the cellular niches as compared to fluid shear stress measured outside of the cellular niches, where the fluid shear stress measured outside of the cellular niches has a peak fluid shear stress of at least about 50 dynes per square centimeter (dynes/cm$^2$), thereby yielding the biomedical implant for use in fluid shear stress environments. All of the disclosures herein relating to the biomedical implant of the present invention also apply to this method of producing the biomedical implant.

With regard to the step of providing an implantable body having a substantially smooth surface, the term "substantially smooth surface" refers to a surface of the implantable body that does not include a pattern of cellular niches (as described herein) formed into the surface, even if the surface does have certain imperfections such as minor indentations (e.g., pock marks or pits) or minor raised portions (e.g., surface specks or protrusions) contained thereon prior to the modifying step of the method. The implantable body can be made of any material suitable for implantation into a subject, with such suitable material being as described elsewhere herein.

In one embodiment, the modifying step of this method involves the following steps: (i) determining the width, the depth, and the spacing dimensions of the plurality of cellular niches sufficient to decrease peak fluid shear stress in and around the cellular niches by between about 5 and about 100% as compared to peak fluid shear stress of the fluid shear stress environment to which the biomedical implant is to be subjected; and (ii) forming a plurality of cellular niches into the substantially smooth surface in order to modify the substantially smooth surface into the patterned surface, where the plurality of cellular niches conform to the dimensions and geometric patterning as determined.

In one embodiment, the determining step of this method further involves identifying the optimal spacing between the cellular niches sufficient to provide a desired growth area within the cellular niches for the layer of living cells. The desired growth area is one that is determined by or in consultation with a biomedical implant designer, a biomedical implant manufacturer, a medical professional who will oversee or conduct the implantation surgery, or the subject. In a particular embodiment, the desired growth area is the growth area sufficient to maximize the area of cell retention on the surface of the biomedical implant.

In another embodiment, this method further involves seeding the patterned surface with cells. The materials, techniques, procedures, and instrumentation for seeding the surface with cells are well known to those of ordinary skill in the relevant art. The types of cells suitable for seeding in accordance with this method are the same types of cells as described herein.

In another aspect, the present invention relates to a method for maintaining at least one localized layer of living cells on a biomedical implant introduced into a fluid shear stress environment of a subject. This method involves the following steps: (i) providing a biomedical implant according to any one of the biomedical implants of the present invention; (ii) seeding the patterned surface with cells of interest so that the cells form at least one localized layer of living cells within the plurality of cellular niches of the biomedical implant; and (iii) introducing the seeded biomedical implant into a fluid shear stress environment of the subject so as to maintain the at least one localized layer of living cells within the plurality of cellular niches by decreasing fluid shear stress within the cellular niches as compared to fluid shear stress measured outside of the cellular niches, where the fluid shear stress measured outside of the cellular niches has a peak fluid shear stress of at least about 50 dynes per square centimeter (dynes/cm$^2$).

In one embodiment of this method, the cellular niches that are formed into the surface of the biomedical implant are effective to decrease peak fluid shear stress within the cellular niches to between about 5 and about 100 percent (%) of the peak fluid shear stress measured outside of the cellular niches.

In another embodiment of this method, either prior to or after the seeding step, the method further involves the step of coating at least a portion of the biomedical implant or at least a portion of the seeded cells with an agent. As used in reference to this method, the term "agent" refers to, but is not limited to, any of the following: a peptide, a protein, a nucleic acid molecule, a cell adhesion molecule, an extracellular matrix (ECM) component, a therapeutic agent, and combinations thereof. Therefore, the term "agent" can include any and all compositions, molecules, and the like that are compatible with the surface of the biomedical implant, the surface of the non-seeded cellular niche, the surface of the seeded cellular niche, the cells seeded on the surface of the biomedical implant and/or within the cellular niche, and/or the subject.

In another embodiment of this method, the cells of interest are effective to release a therapeutic agent after introducing the seeded biomedical implant into the subject. In a particular embodiment, the therapeutic agent is released at the surface of the cellular niche and/or through pores formed into the interior surface of the cellular niche (e.g., pores that open further into the body of the biomedical implant). In another embodiment, the cells of interest can be, for example, endothelial cells that have been modified to express growth factors (e.g., VEGF) or growth inhibitors in order to produced a desired therapeutic or diagnostic effect in the subject (e.g., assist in healing a wound, assist in acceptance of an implant, etc.).

As described herein, the present invention allows for the generation of cellularized niches that can interface biologically while being protected mechanically. Fluid contacting surfaces offer ideal environments for the application of the technology of the present invention. Two non-limiting applications of the use of the technology of the present invention include, without limitation, cardiovascular implants and renal filtration. Fluid flows over the surface of implants in these two areas induce shear stress on the surface of the devices, inhibiting their coating with cells.

Current biomedical devices in these two areas have limited optimization to reflect the natural tissue they are replacing. While there is little rejection from the body upon device implantation, the biological impact is limited to the direct application of the implant. For example, the prosthetic heart valve functions to control blood flow through the cardiac cycle allowing the left ventricle to properly pump blood to the body. Outside of this primary purpose, current aortic valve (AV) replacements do not interact with the body. A simple optimization of cardiac devices would be applying an endothelial cell coating. Endothelial cells line the cardiovascular system, thus, this application would allow patients to decrease the dosage of anti-thrombotic drug therapy.

When examining the renal filtration devices for patients on dialysis it has been found that there is a significant nutrient loss that could be avoided with an active cellular filtration system. The present invention would allow for the application of a cellular layer on renal filtration systems; specifically, epithelial cells could be seeded on a filter membrane, and then protected by the application of the cellular niche patterning of the present invention. This application would allow for the cellular uptake of nutrients, decreasing nutrient waste while the epithelial cells are protected from shear and preventing platelet induced passivation.

In another aspect, the present invention also allows for the direct application of drugs to specific cell locations. Endothelial cells seeded on the surface of cardiovascular devices can be elicited to secrete certain biological factors with different chemical signals. While many such chemical signals have an adverse systemic effect, the localized application of the drug can have profound effects on the efficacy of the implant. Specifically, for example, if a drug that caused endothelial cells to secrete anti-thrombotic factors was contained within the prosthetic heart valve that was now seeded with cells, one may be able to overcome the need for concurrent anti-coagulant therapies altogether.

As described herein, various features of embodiments of the present invention include surface geometry modification and drug elution. Each of these features is further described herein below.

Surface Geometry Modification:

In one aspect, the present invention produces cellular niches via the surface modification of implant materials. The present invention provides surface modification of implants to protect cells from shear stresses while allowing the cells to interact directly with biological factors. This protected yet natural environment allows the cells to secrete factors that assist with wound healing and promote the long-term function of the implant device.

An alternative embodiment of the present invention would be to create cellular niches that control cell-based basal secretion to underlying cells, as in through a filter mesh to which cells are adhered. This application would allow for cellular protection from passing food while allowing the digestive fluids to be produced from the cellular coating. Similarly, the technology of the present invention can be applied to the renal filtration system. Instead of having cells secrete digestive enzymes they would uptake nutrients promoting more effective dialysis.

High shear stress environments in the body are mainly limited to flowing fluid systems. While one aspect of this invention is focused on decreasing the shear that is present in flow conditions it also is capable of producing cellular niches beneficial for generating specific cell types from stem cells. Thus, the present invention can also be used in a range of biomedical applications.

Drug Elution:

With specialized cellular niches on the surface of biomedical implants, cells can be targeted with drug therapies. Specific drugs can be contained within the implant that target the cell types seeded within the cellular niches. This specified application of the drug allows for minimized drug dosing as cells are directly exposed to the drug. The direct exposure decreases the likelihood of inadvertent exposure of other cells types maximizing the drug's potential. This isolated drug application can have significant affect in the drug efficacy while having little to no adverse effects.

The surface modifications of the present invention have broad applications with multifunctional uses. The following are additional aspects of the present invention, including, without limitation: (i) uniform or non-uniform niche geometry (curved wells, curved surfaces, nonlinear traversing, different depths, fillets, heterogeneous well spacing and widths, etc.); (ii) filters placed underneath for cell mediated delivery of signals into substrata or filtration of circulating molecules; (iii) delivery of drugs through filters for local effects (cell or tissue level); and (iv) drugs released from within the sidewalls (where cells are not attached and may therefore not be exposed).

EXAMPLES

The following examples are intended to illustrate particular embodiments of the present invention, but are by no means intended to limit the scope of the present invention.

Example 1

Cellular Niche Generation Via Micro-Patterning of Biomedical Implants

This example describes one embodiment of a biomedical implant according to the present invention. Given that one goal of the present invention was to develop way to decrease fluid shear stress, a prototype of the present invention has been developed for a prosthetic heart valve. The prototype itself is made of material that resembles synthetic heart valves, and was simplified to a square shape for ease of development and testing.

Figure 1:
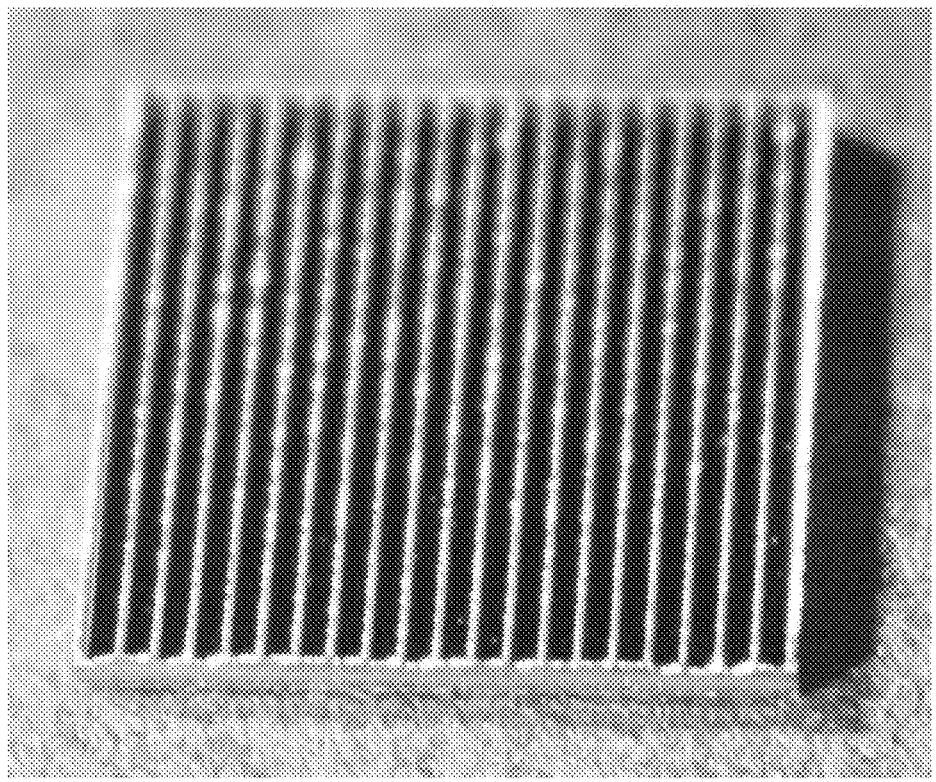
FIG. 1 is a photograph of a patterning prototype of one embodiment of an etched mechanical heart valve design of the present invention.
Figure 2:
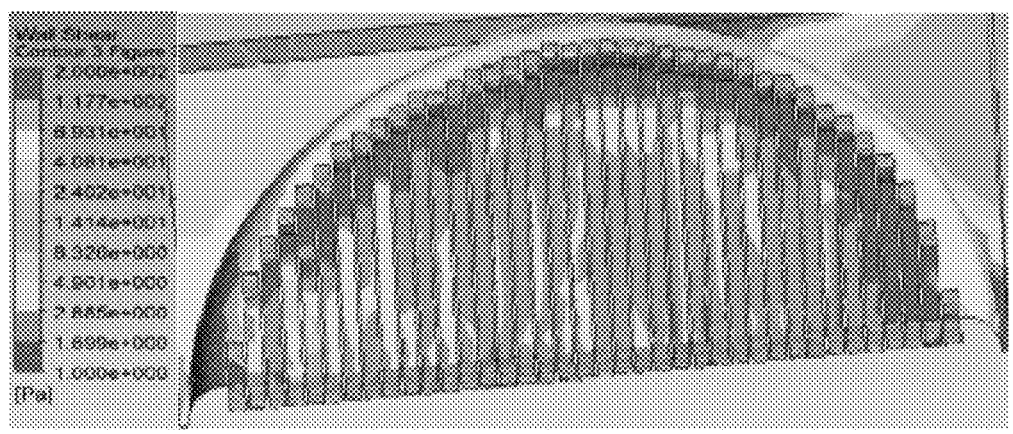
FIG. 2 is a picture showing a CAD analysis of shear stresses on the surface of an etched prosthetic heart valve in an implanted simulation.

The material used to generate the sample was a 4" Silicon wafer that was 1000 um thick; 1 cm×1 cm chips were made for testing out of the 4" wafer (FIG. 1). The pattern to be etched into the silicon was developed following CAD analysis of blood flow over etched surfaces. This geometry was chosen in particular because of its ability to decrease the shear stress caused by blood to levels within a range where endothelial cells can function normally.

Optimization of the etched geometry was done via CAD analysis to find a depth, width and spacing that maximized cell growth area on each valve, while maintaining ideal fluid flow exposure to cells. Previous work had identified the maximum amount of shear stress that endothelial cells could remain adhered to the surface at 20 dynes/cm$^2$. We also wanted the cells to remain exposed to shear stress above 1 dynes/cm$^2$ as endothelial cells need to be exposed to shear to function properly.

In one embodiment of the present invention, the developed geometry for cardiovascular application has a depth of 700 um, a spacing of 75 um, and a channel width of 400 um (see, e.g., FIG. 3).

To develop the prototype, a technique able to precisely cut into silicon wafers was needed. To have an exact well geometry etched into the surface of the heart valve with precise replication and patterning, we utilized nano-fabrication tools from Cornell's center for nano-fabrication. Specifically, after designing a pattern mask plasma the silicon wafer was etched using an Oerlikon etcher until a depth of 700 um had been achieved. Other means for making the niches can include built up rather than etching out approaches.

Figure 14:
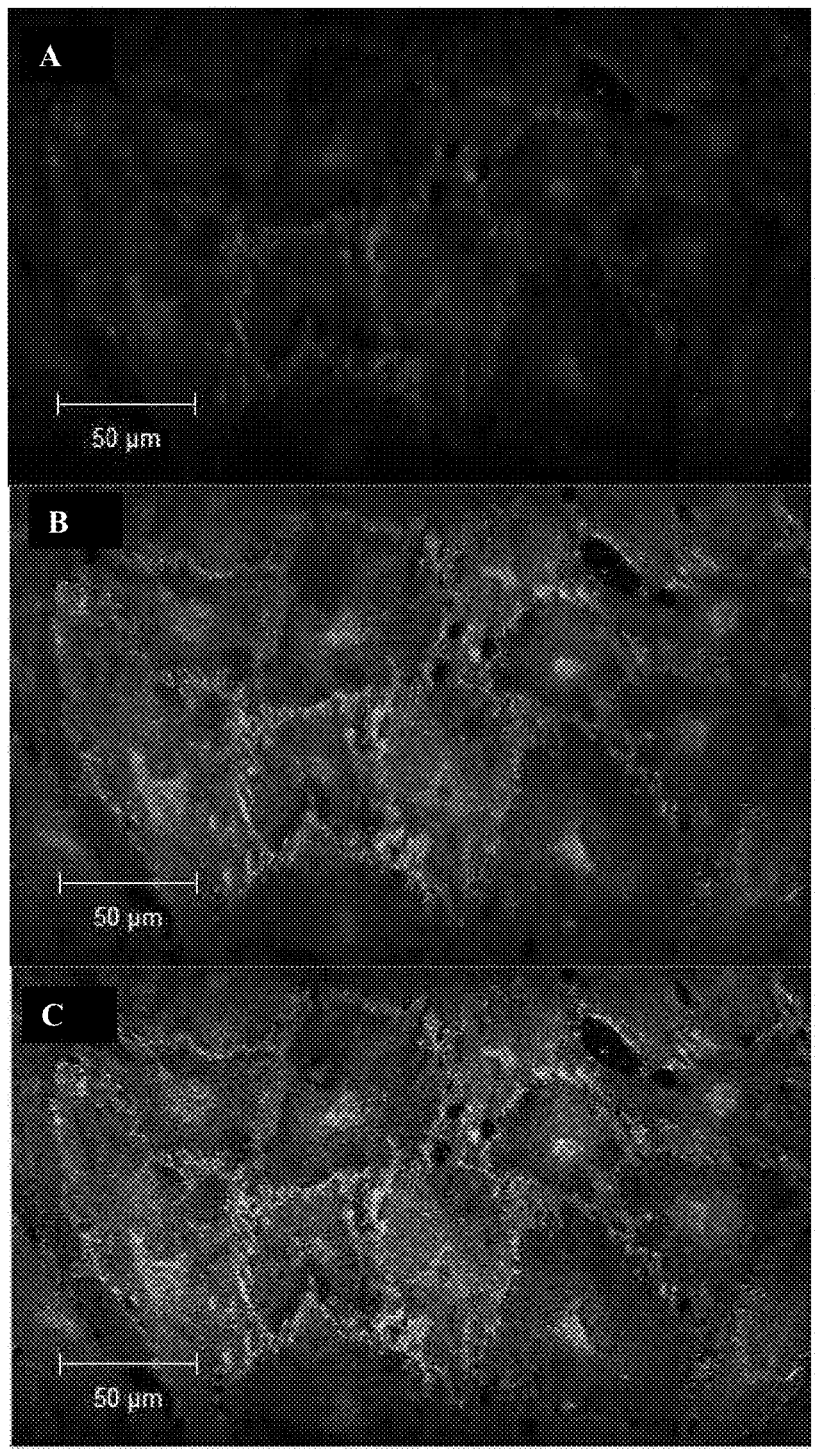
FIGS. 14A-14C are photographs of cell survival tests of cells on one embodiment of a patterned surface of the present invention at 200+ dynes/cm². PAVECs after 48 hrs of 200+ dynes/cm² shear exposure on etched surface expressing both endothelial and antithrombotic phenotypes.

To verify the functionality of the present invention, the etched samples were exposed to high shear conditions and cellular presence determined via antibody staining. After etched samples were incubated with adhesion proteins for an hour, blocked in milk for an hour and seeded with porcine aortic valve endothelial cells for an hour, they were exposed to 48 hours of 200+ dyne/cm$^2$ shears. There was clear endothelial presence, proving that the shear was able to be decreased such that endothelial cells could survive (see, e.g., FIGS. 14A-14C).

Figure 4:
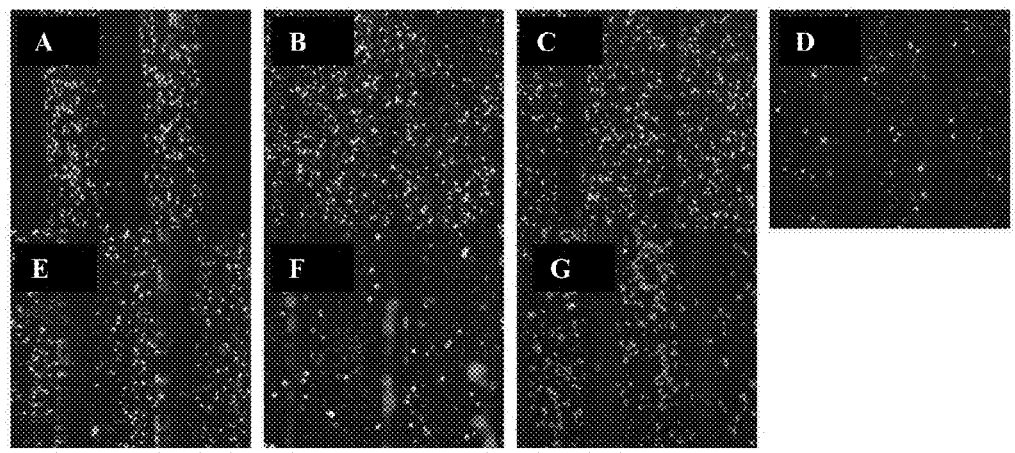
FIGS. 4A-4G are photographs showing results of a platelet adhesion test: platelets taged with green cell tracker and PAVECs tagged with red cell tracker. Sample conditions are shown as follows.

To verify our initial hypothesis that patients would require less anti-coagulant therapies using the surface modified biomedical implant of the present invention, a platelet adhesion assay was conducted. In this assay four test conditions were examined, as follows: (1) etched carbon coated silicon (surface properties identical to mechanical heart valve); (2) test condition 1 plus adherent proteins; (3) test condition 2 plus porcine aortic valve endothelial cells; and (4) test condition 3 plus 48 hours of shear exposure. The two adhesion proteins that were examined were collagen and fibronectin. All the samples were covered in a platelet solution and allowed to incubate for 10 minutes. The test results show a significant decrease in platelet adhesion upon seeding with cells and again a significant decrease in platelet adhesion with shear exposure to the cells (see FIG. 4).

Example 2

Mechanical Heart Valve Surface Optimization for Endothelial Cell Adhesion

Endothelial cells line the vascular system of the human body. Current heart transplant options do not incorporate this vital vascular lining; endothelialization. Biological valves pose little foreign body response from the immune system and can be implanted with little drug assistance, but their drawback is that they require replacement within ten years due to wear. Mechanical heart valves are the alternative as they last forever. The drawback in this case is intense foreign body response from the host; thus, harsh anticoagulants such as warfarin are required for patients with these types of implants. This example was conducted to directly address the problem of endothelialization by seeding endothelial cells onto the surfaces of aortic heart valve implants. The findings show that it is possible to adhere endothelial cells to the surfaces of implanted heart valves, and that with proper topographical adjustments the endothelial cells can remain adhered to the surface of the heart valves in high shear environments. This example provides proof of concept for the endothelialization of vascular implants.

This example was aimed at developing a mechanical valve coated with endothelial cells such that there is no need for blood thinners. Endothelial cells secrete antithrombotic factors that prevent blood from clotting, thus, it was hypothesized that by coating the mechanical valve with endothelial cells one could prevent the need for blood thinners post mechanical valve implantation. To adhere endothelial cells to the surface of mechanical heart valves, the maximal shear resistances of various protein matrixes was examined. Upon identifying the maximal shear that could be withstood by the adhesion proteins, a topological geometry was developed via CAD analysis to decrease the shear stress induced by blood flow over the surfaces of the valves. Upon microfabricating the identified geometry onto the surface of silicon wafers, the viability of cells on the surface under high shear forces was examined.

Materials and Methods

Cell Culture

Porcine Aortic valve endothelial cells (PAVEC) were isolated from healthy porcine aortic valves were via collagenase digestion as previously described (5, 6). PAVECs were cultured in Dulbecco's Modified Eagle's Medium (Gibco) supplemented with 10% fetal bovine serum (Invitrogen), 3.7 g/L sodium bicarbonate (Cell Grow), 1% penicillin-streptomycin (Gibco), and 50 mg/L heparin salts (Sigma Aldrich). Cells were grown at 37° C. and 5% $CO_2$ and used between passage number 3 and 5.

Cell Seeding on Valve Surface

Our previous work has identified the surface chemistry of the Medtronic disk mechanical heart valve to be identical to electron beam carbon coated silicon chips (7). Briefly, using a four inch silicon wafer (Silicon Quest) we generated 1 cm by 1 cm carbon coated (CVC SC4500 Evaporator, Cornell CNF) chips; representative of mechanical heart valve surfaces.

Our developed seeding technique (7) consists of steam sterilization of the chips followed by a one hour room temperature incubation of adhesion matrix [Type 1Collagen (BD Biosciences), or Human Fibronectin (BD Biosciences)]. This was followed by a one hour room temperature blocking in 5% non fat dry milk, and subsequent hour cell seeing at 10,000 cells/chip suspended in 50 ul of media. The cell seeded chips were then enclosed in the parallel plate flow bioreactor that has been previously described (8).

Parallel Plate Shear Testing

Adhesion matrix test samples were exposed to 48 hour shear stress using a Masterflex cartilage peristaltic pump (Cole-Parmer). The bioreactor was developed to expose the samples to 2, 10, and 20 dynes/cm$^2$ of shear stress in one of the three channels respectively.

Characterization of Endothelial Phenotype

After 48 hours of shear testing, samples were immediately fixed in either 4% PFA or methanol. Samples fixed in PFA were permeabalized with 0.2% Triton X (BD) for 10 minutes at room temp, the day the staining procedure was implemented. All fixed samples were kept in PBS until being blocked with 1% BSA overnight in 4° C. (Rockland) prior to staining with primary antibodies. Samples were characterized by staining with primary antibodies at a concentration 1:4000 in PBS overnight in 4° C.: mouse anti pig CD31 (AbD Serotech), rat ant pig CD 144 (AbD Serotech) and/or mouse anti human eNOS (BD Transduction Laboratories). Three rinses of the samples with PBS occurred prior to the addition of secondaries. The secondary antibodies were used at 1:400 in 1% BSA for 2.5 hr at room temperature, goat anti mouse IgG Alexaflour 488 (Invitrogen), goat anti mouse IgG Alexaflour 568 (Invitrogen), and goat anti rat IgG 568 (Invitrogen). Nuclear staining was done using a concentration 1:10,000 in sterile water Hoechst 33342 (Invitrogen) for 15 minutes at room temperature. Again the samples were washed three times with PBS then stored in PBS until imaging. Imaging occurred with 4 hours of staining with secondary antibodies using a Zeiss confocal microscope (CoresLifesciences Cornell).

CAD Design Generation

Ansys fluent was used to generate a computer model of blood flow over the surface of a prosthetic heart valve. The model considered blood a Newtonian fluid with a viscosity of 0.0037 Pa·sec and a density of 1060 kg/m$^3$ (9). Using this model a geometry was developed such that the shear stress in the bottom of the developed wells would be below 10 dynes/cm$^2$. For assessing the shear in the bioreactor we used a viscosity of 0.00095 Pa sec and a density of 1000 kg/m$^2$ (10).

Micro-Fabrication of Generated Micropattern on Silicon Chips

The designed pattern was etched using an Oerlikon etcher (Cornell CNF) into a 1 mm thick silicon wafer (SVM). The pattern was developed such that for each 4" wafer multiple 1 cm by 1 cm chips would be generated. Once the 4" wafer was etched with replicate patterns the chips were separated into individual 1 cm by 1 cm samples using a dicing saw KS 7100 (Cornell CNF).

Fluid Shear Stress Verification in Bioreactor

To identify the fluid shear stress being exposed to the samples, and to verify the shear at the bottom of the well 9.7±0.4 um polymer microspheres (Thermo Scientific) were added to the culture media and recorded under 80, 160, 320 ml/min flow rates with only the center channel of the bioreactor allowing fluid flow. The bead flow in the channel bottoms was captured using a Nikon SMZ1000 stereomicroscope and a Sony DXC_390 camera. The digital recording program used was streampix with a pixeLinke videoconverter. The file was converted using virtual dub 1.6.14 and bead velocity was measured using Image J.

High Shear Testing of Micropatterned Valve Surface

The micropatterened chips were coated with carbon, and seeded with cells as described above. The samples were then put into a modified version of the bioreactor used to identify adhesion protein strength enhancing the shear stress by restricting the flow of fluid to only the center channel of the three channels. Samples were run at maximal flow rate through the peristaltic pump to maximize the shear exposed in the bioreactor.

Cell Tracking

Cell tracker red CMTPX (Invitrogen) was used for short [<1 hr] experiments, specifically the high shear testing of the micropatterned chips, to verify cell presence. The stained cells were visualized using a Zeiss stereomicroscope fitted with a Texas-red fluorescence filter. Images were captured using ImagePro and analyzed using ImageJ.

Results

Endothelial Cell Viability Under Prolonged Shear

Figure 5:
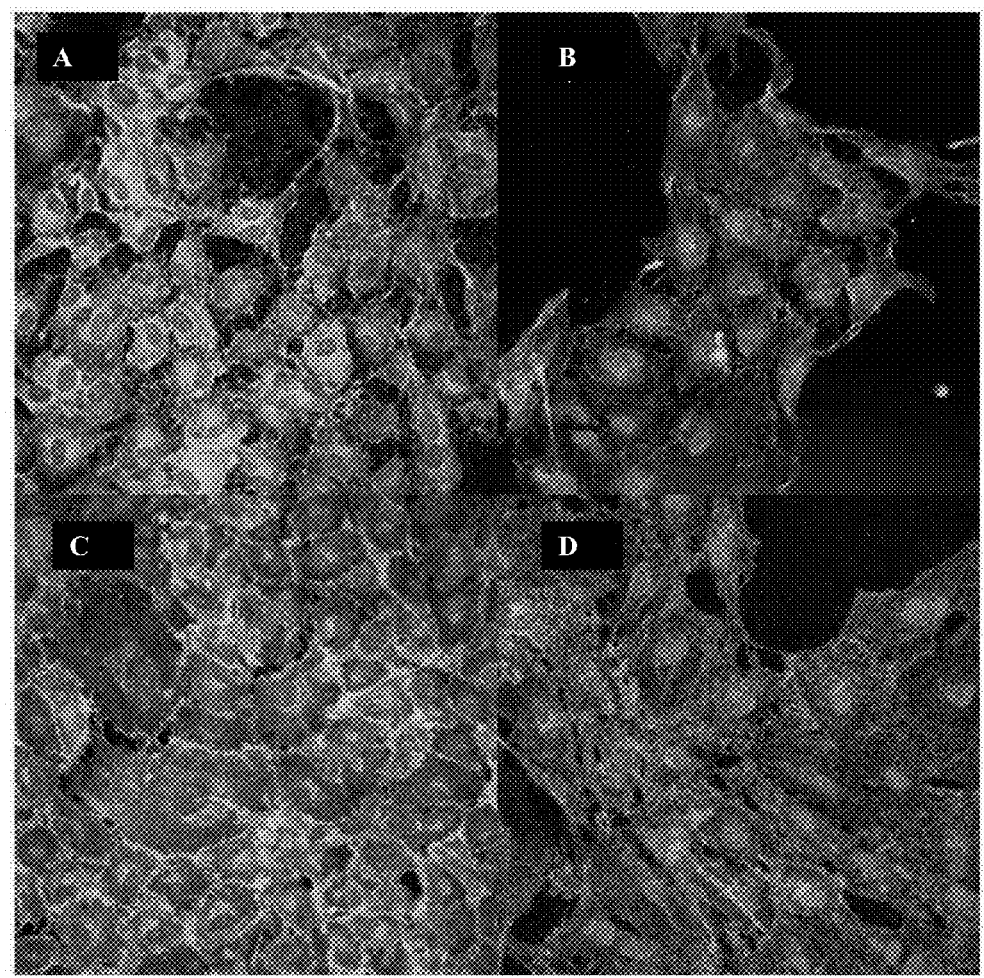
FIGS. 5A-5D are photographs showing results of endothelial cell viability tests on a surface of an embodiment of a heart valve of the present invention: Blue:Hoechst Red:CD 144 Green:eNOS
Figure 6:
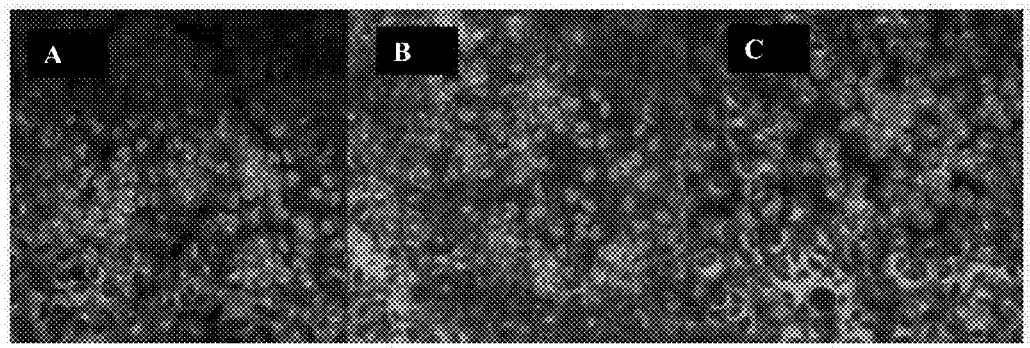
FIGS. 6A-6C are photographs showing results of endothelial cell viability tests on a surface of an embodiment of a heart valve of the present invention: Blue:Hoechst Green:CD31 Collagen matrix with endothelial cells exposed to 2 dynes/cm² (FIG. 6A); 10 dynes/cm² (FIG. 6B); 20 dynes/cm² (FIG. 6C) for 48 hours.

In our testing to verify that endothelial cells maintained their phenotype, and remained adhered to the surfaces of the heart valves we examined collagen and fibronectin adhesion matrixes. Our results showed the presence of endothelial cells after 48 hours of exposure to 2, 10, and 20 dynes/cm$^2$ of shear forces in both collagen and fibronectin samples (FIG. 5). While the only chips that contained any cells on their surface for the collagen experiment were in the low shear channel, we have previous data showing that cells can survive the 48 hour shear exposure (FIG. 6).

Fluid Shear Stress Decrease on Surface of Valve

In developing the geometry for decreasing the shear stress of the blood flowing over the top of the valve we applied 'corduroy' patterns to the surface of the valve (FIG. 7).

To identify the depth and the width between each of the 'corduroy' walls we examined two dimensional flow analysis. Specifically, we identified the shear at the bottom of our CAD developed wells based on depth and width alterations. Our testing showed an overall correlation between all the data-points (FIG. 8).

Figure 9:
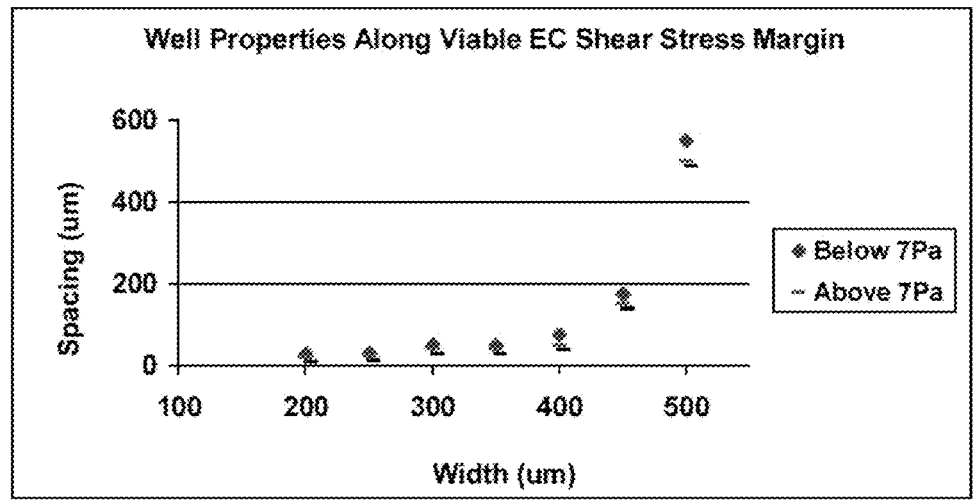
FIG. 9 is a graph showing optimization of spacing for 3-d channels with flow perpendicular.

From this compiled data we selected 700 um as our target depth and began examining the spacing between the ridges to find the ideal total geometry. In examining the width vs spacing we found that there was a limit of 400 um width before the spacing would have to be increased dramatically (FIG. 9).

With the depth and width set, we had to optimize the spacing for the channels such that we could maximize the area for the cells to grow in at the bottom of the well. Table 1 shows relative comparisons of the final dimensional analysis.

TABLE 1

Identification of Depth: 700 um, Width 400 um, and Spacing 75 um by maximizing width and EC growth area

| Depth (um) | Width (um) | Spacing (um) | Area for EC (um)$^2$ |
| --- | --- | --- | --- |
| 700 | 200 | 30 | 87600 |
| 700 | 250 | 30 | 89250 |
| 700 | 300 | 50 | 85500 |
| 700 | 350 | 50 | 87500 |
| 700 | 400 | 75 | 84000 |
| 700 | 450 | 175 | 72000 |
| 700 | 500 | 550 | 74000 |

Figure 10:
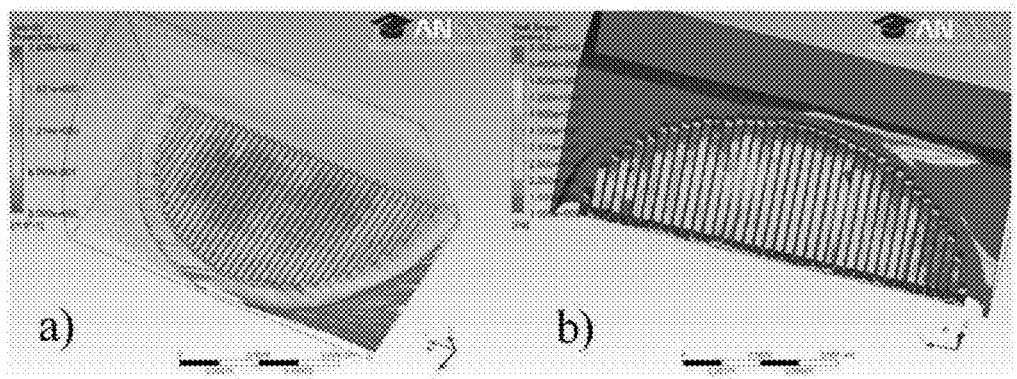
FIGS. 10A-10B are pictures showing a CAD analysis of shear stresses on the surface of an etched prosthetic heart valve in an implanted simulation.

Having identified these parameters for our geometry we were now in need of ensuring that the calculations concurred with the developed shape. To assess this, a three dimensional analysis of the etched pattern into the surface of a heart valve with full blood flow through the aortic valve was simulated. The etched wells contained the parameters of the developed 'ideals' and the fluent analysis needed to reduce the shear in the wells of the heart valve to within the range that our long term studies had shown cells could survive in (below 15 dynes/cm$^2$). FIG. 10 shows the shears as well as the flow rate in and over the wells respectively.

Figure 11:
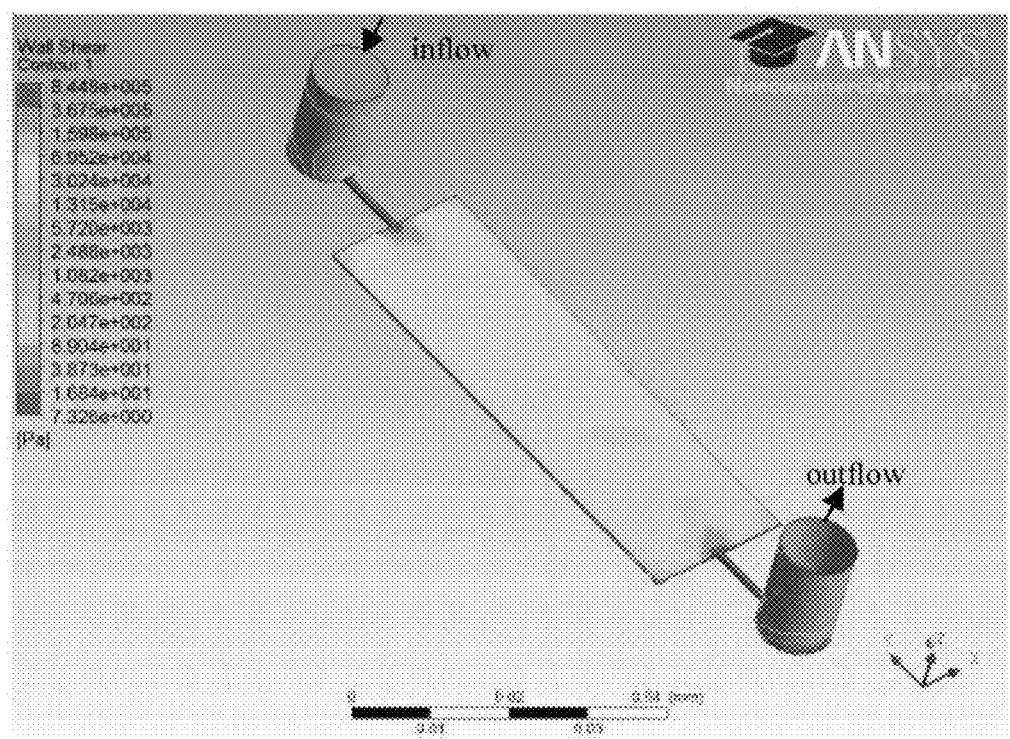
FIG. 11 is a picture showing shear through a bioreactor chamber under 70 ml/min of flow. Fluid enters down the top cylinder across the testing surface then up and out of the bottom canister.

In examining the maximal shear stress within our bioreactor we simplified the geometry such that flow was entering through only the middle channel. FIG. 11 depicts the relative shear through the bioreactor under 70 ml/minute flow.

Micro Pattern Generation on the Surface of the Heart Valves

Figure 12:
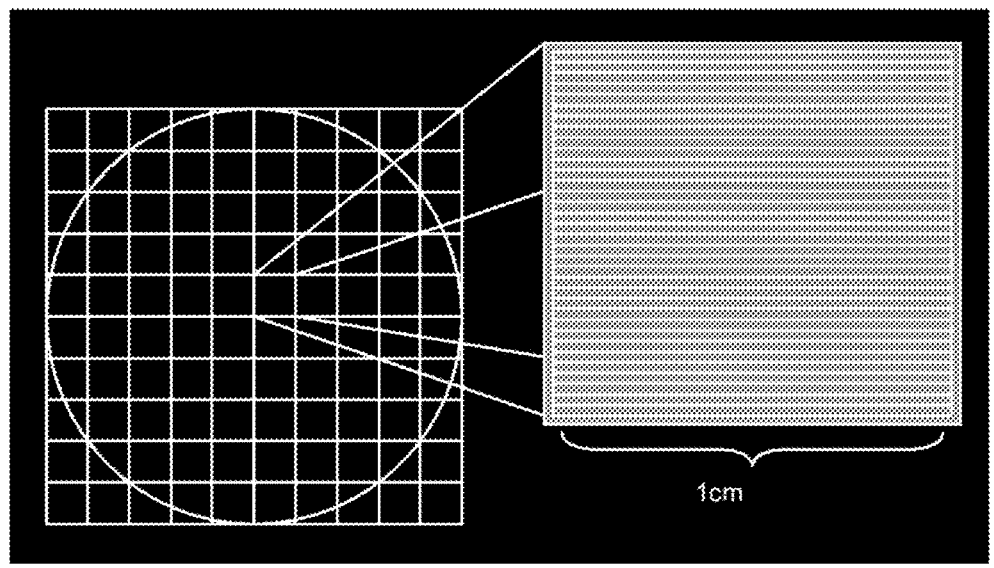
FIG. 12 is a picture depicting how a 4" wafer would be sectioned to generate multiple 1×1 cm squared to be used for testing in the bioreactor.

To maximize the number of samples we generated from each four inch silicon wafer we stayed with our 1 cm by 1 cm chip size. To divide the wafer we developed an etching model that is depicted in FIG. 12. This process allowed us to generate the maximum number of samples per wafer and would correlate to our previous studies as the samples would fit in the developed bioreactor.

The wafers were developed in the Cornell Center for Nanoscale Fabrication. The etching process was a success; with the developed wafers having the proper well geometries. In the first run we had difficulties sectioning the chips, thus our preliminary studies were run with irregularly shaped samples. We have optimized the sample generation process; specifically, cutting the wafers with a dicing saw, and are now able to produce exactly 1 cm by 1 cm squares with clean cuts along the margins.

Fluid Shear Stress Verification in Bioreactor

Micro bead infused media was run through the bioreactor at varying rates to determine the maximal flow rate possible through our bioreactor system. We were able to induce flows of 80 ml/min, 160 ml/min, and 320 ml/min to flow through the bioreactor system. While our imaging devices were not advanced enough to capture the bulk flowrate across the surface of the etched chips, we were able to visualize flowpatterns, and identify the velocity of the fluid in the bottom of the wells (Table 2).

TABLE 2

Flow velocity in well bottoms compared to flow rate in bioreactor

| Velocity (mm/sec) | Flow Rate (ml/min) |
|---|---|
| 3.20 | 80 |
| 2.56 | 160 |
| 2.13 | 320 |

High Shear Test of Micropatterned Chips

Figure 13:
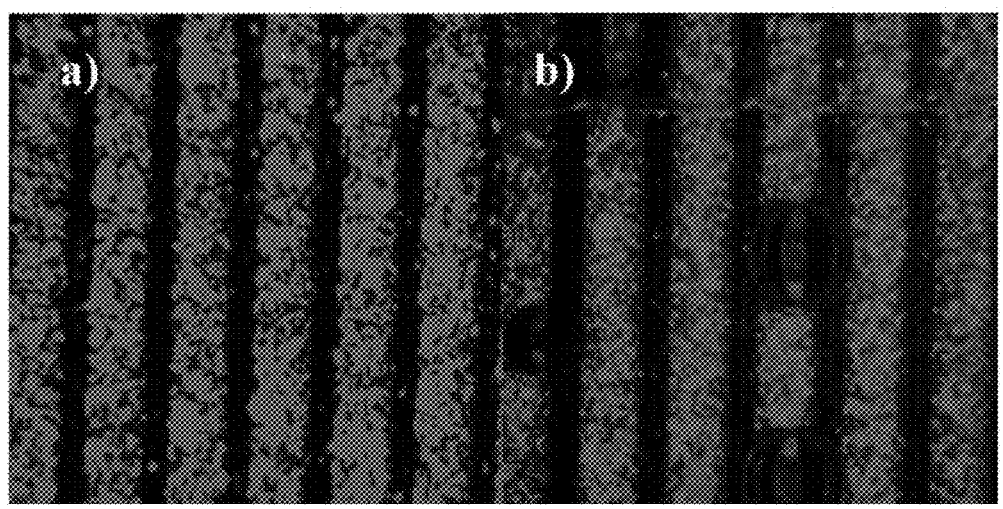
FIGS. 13A-13B are photographs showing results of high shear testing of one embodiment of a patterned surface of the present invention.

To identify the presence of cells in micropatterend wells under high shear stress we stained our cells with cell tracker red during seeding and monitored cell presence under high shear flow rates. Cells remained adhered under 80 ml/min of flow for over 20 minutes (FIG. 13).

Discussion

This study aimed to identify a surface geometry for mechanical heart valve implants that would promote the survival of endothelial cells. Through phenotype testing at low shear stresses, computer aided design simulation of blood flow over heart valves, and high shear stress exposure experiments, we were able to prove proof of concept that it is possible to seed endothelial cells onto the surfaces of valves and they can withstand high shear forces.

The majority of this study was focused around modifying existing protocols and developing new protocols that would allow for the generation of data that will conclusively prove (or disprove) the viability of using micropatterened surfaces for the endothelialization of heart valve implants. This study also sets the stage for identifying the properties of endothelial cells relative to shear exposure; specifically the relative power of an endothelial layer to control the clotting cascade.

REFERENCES

Citation of a reference herein shall not be construed as an admission that such reference is prior art to the present invention. All references cited herein are hereby incorporated by reference in their entirety. Below is a listing of various references cited herein:

1. Broze G J. Tissue factor pathway inhibitor and the revised theory of coagulation. *Annual Review of Medicine* 46:103-112 (1995)
2. Furie B, Furie B C. Mechanisms of thrombus formation. *New England Journal of Medicine* 359: 938-949 (2008)
3. White T A, Johnson T, Zarzhevasky N, Torn C, Delcrolx S, Holroyd E W, Maroney S A, Singh R, Pan S, Fay W P, van Deursen J, Mast A E, Sandhu G S, Simari R D. Endothelial-derived tissue factor pathway inhibitor regulates arterial thromosis but is not required for development or hemostasis. *Blood* 116: 1787-1794 (2010).
4. Ming Z, Hu Y, Xiang J, Polewaski, Newman P, Newman D K. Lyn and PECAM-1 function as interdependent inhibitors of platelet aggregation. *Blood* 117: 3902-3906 (2011)
5. Butcher, J. T., Penrod, A. M., Garcia, A. J., and Nerem, R. M. Unique morphology and focal adhesion development of valvular endothelial cells in static and fluid flow environments. Arterioscler. Thromb. Vasc. Biol. 24, 1429, 2004.
6. Butcher, J. T., and Nerem, R. M. Porcine aortic valve interstitial cells in three-dimensional culture: comparison of phenotype with aortic smooth muscle cells. J. Heart Valve Dis. 13, 478, 2004.
7. Tucker S, Frendl C, Garcia A, Butcher J. A high throughput assay for evaluating the shear resistance of endothelialized mechanical heart valve prostheses. *IN PRESS.*
8. Butcher J T, Nerem R M. Valvular endothelial cells regulare the phenotype of interstitial cells in co-culture: effects of steady shear stress. *Tissue Engineering.* 12: 905-915 (2006).
9. Frauenfelder T, Boutsianis E, Schertler T, Husmmann L, Leschka S, Poulikakos D, Marincek B, Alkadhi H. Flow and wall shear stress in end-to-side and side-to-side anastomosis of venous coronary artery bypass grafts. *BioMedical Engineering OnLine* 6:35 (2007).
10. Kaya M, Gregory T S, Dayton P A. Changes in lipid encapsulated microbubble population during continuous infusion and methods to maintain consistency. *Ultrasound Medical Biology* 35: 1748-1755 (2009).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A biomedical implant for use in a fluid shear stress environment of a subject, said biomedical implant comprising:
    a patterned surface having a plurality of cellular niches effective to maintain at least one localized layer of living cells within the plurality of cellular niches by decreasing fluid shear stress within the cellular niches as compared to fluid shear stress measured outside of the cellular niches, said cellular niches being effective to decrease peak fluid shear stress within the cellular niches to between about 5 and about 100 percent (%) of peak fluid shear stress measured outside of the cellular niches,
    wherein each cellular niche comprises a crevice formed into the surface of the biomedical implant, each crevice having (i) a top, open end located at the surface of the biomedical implant, (ii) a bottom, substantially closed end located at a region furthest below the surface of the biomedical implant, and (iii) opposing sidewalls that extend from the top end to the bottom end of the crevice, and wherein each crevice has a depth and width sufficient to maintain and retain a plurality of viable cells within the crevice, including at the bottom of the crevice and/or on one or more of the sidewalls of the crevice, said depth of each crevice being between about 100-1500 microns (μm) and said width of each crevice being between about 100-1000 μm, and wherein spacing between each cellular niche is between about 1-600 μm.

2. The biomedical implant according to claim 1, wherein the width measured between opposing sidewalls can be the same or different throughout the length and/or height of the crevice.

3. The biomedical implant according to claim 1, wherein the fluid shear stress measured outside of the cellular niches has a peak fluid shear stress selected from the group consisting of greater than at least about 50 dynes per square centimeter (dynes/cm$^2$), greater than at least about 60 dynes/cm$^2$, greater than at least about 100 dynes/cm$^2$, greater than at least about 150 dynes/cm$^2$, greater than at least about 200 dynes/cm$^2$, greater than at least about 300 dynes/cm$^2$, greater than at least about 400 dynes/cm$^2$, greater than at least about 500 dynes/cm$^2$, greater than at least about 600 dynes/cm$^2$, greater than at least about 700 dynes/cm$^2$, greater than at least about 800 dynes/cm$^2$, greater than at least about 900 dynes/cm$^2$, greater than at least about 1,000 dynes/cm$^2$, greater than at least about 1,250 dynes/cm$^2$, greater than at least about 1,500 dynes/cm$^2$, greater than at least about 1,750 dynes/cm$^2$, and greater than at least about 2,000 dynes/cm$^2$.

4. The biomedical implant according to claim 1, wherein the fluid shear stress measured outside of the cellular niches has a peak fluid shear stress of between about 60-2,000 dynes/cm$^2$.

5. The biomedical implant according to claim 1, wherein the bottom of the cellular niche is a substantially planar surface or a non-planar surface selected from the group consisting of a flat surface, a concave surface, a convex surface, a filleted surface, a chamfered edged surface, a curved edged surface, and combinations thereof.

6. The biomedical implant according to claim 1, wherein said biomedical implant is made of a material selected from the group consisting of a metal, a plastic, a polymeric material, glass, silicon, and the like.

7. The biomedical implant according to claim 1, wherein said biomedical implant is coated with a coating material selected from the group consisting of a carbon, a metal alloy, synthetic polymer, silicon, and the like.

8. The biomedical implant according to claim 1, wherein said cells are selected from the group consisting of endothelial cells, endocardial cells, epithelial-like cells, and the like.

9. The biomedical implant according to claim 1, wherein said biomedical implant is a heart valve, a device for pancreatic regulation of insulin, a hemofiltration device, a catheter delivered blood contacting device, a stent, a prosthetic vascular graft, and a cardiovascular patch.

10. The biomedical implant according to claim 1, wherein said cellular niches are porous, solid, or a combination thereof.

11. A biomedical implant system for use in fluid shear stress environments of a subject, said system comprising:
- a biomedical implant according to claim 1; and
- a plurality of cells seeded on at least a portion of the patterned surface of said biomedical implant, wherein said plurality of cells can comprise the same or different types of cells.

* * * * *